(12) United States Patent
Liang et al.

(10) Patent No.: US 10,370,659 B2
(45) Date of Patent: Aug. 6, 2019

(54) COMPOUNDS AND METHODS FOR INCREASING ANTISENSE ACTIVITY

(71) Applicant: Ionis Pharmaceuticals, Inc., Carlsbad, CA (US)

(72) Inventors: Xue-hai Liang, Del Mar, CA (US); Wen Shen, Carlsbad, CA (US); Stanley T. Crooke, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/552,725

(22) PCT Filed: Feb. 23, 2016

(86) PCT No.: PCT/US2016/019165
§ 371 (c)(1),
(2) Date: Aug. 22, 2017

(87) PCT Pub. No.: WO2016/138017
PCT Pub. Date: Sep. 1, 2016

(65) Prior Publication Data
US 2018/0148718 A1 May 31, 2018

Related U.S. Application Data

(60) Provisional application No. 62/119,709, filed on Feb. 23, 2015.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/113* | (2010.01) | |
| *A61K 31/7125* | (2006.01) | |
| *G01N 33/53* | (2006.01) | |
| *C12N 15/11* | (2006.01) | |
| *C07K 14/47* | (2006.01) | |
| *C12Q 1/6876* | (2018.01) | |

(52) U.S. Cl.
CPC ........ *C12N 15/113* (2013.01); *A61K 31/7125* (2013.01); *C07K 14/47* (2013.01); *C12N 15/111* (2013.01); *C12Q 1/6876* (2013.01); *G01N 33/5308* (2013.01); *C12N 2310/11* (2013.01); *C12N 2310/113* (2013.01); *C12N 2310/14* (2013.01); *C12N 2310/315* (2013.01); *C12N 2310/321* (2013.01); *C12N 2310/335* (2013.01); *C12N 2310/3341* (2013.01); *C12N 2310/341* (2013.01); *C12N 2310/351* (2013.01); *C12N 2310/3517* (2013.01); *C12N 2320/50* (2013.01); *C12Q 2600/158* (2013.01); *G01N 2500/04* (2013.01)

(58) Field of Classification Search
CPC .... C12N 15/113; C12N 15/111; A61K 31/713
See application file for complete search history.

(56) References Cited

U.S. PATENT DOCUMENTS 5,734,039 A * 3/1998 Calabretta .......... C12N 15/1135
536/24.5
2007/0254329 A1 * 11/2007 Rubin .................... C07K 14/47
435/29

FOREIGN PATENT DOCUMENTS

WO WO 2013/192233 12/2013

OTHER PUBLICATIONS

Leonetti et al. (Current Pharmaceutical Design, 2007, 13, 5, pp. 463-470).*
Li et al. (Cancer Research, 63, 3268-3274, 2003).*
Stains et al. (Biochem. J., 2005, 385, 613-623).*
Dong et al. (Mol Endocrinol, Aug. 2009, 23(8), 1147-1160).*
Sasaki et al. (PNAS, Feb. 2009, vol. 106, No. 8, pp. 2525-2530).*
Quiskamp et al. (Cell. Mol. Life Sci., 2014, 71, 311-329).*
Abdul-Manan et al., "hnRNP A1 binds promiscuously to oligoribonucleotides: utilization of random and homo-oligonucleotides to discriminate sequence from base-specific binding" Nucleic Acids Res. (1996) 24(20): 4063-4070.
Bachmann et al., "Characterization of the autoantigen La as a nucleic acid-dependent ATPase/dATPase with melting properties" Cell (1990) 60(1): 85-93.
Bayfield et al., "Conservation of a masked nuclear export activity of La proteins and its effects on tRNA maturation" Mol Cell Biol (2007) 27(9): 3303-3312.
Beltinger et al., "Binding, uptake, and intracellular trafficking of phosphorothioate-modified oligodeoxynucleotides" J. Clin. Invest. (1995) 95(4): 1814-1823.
Bennett et al., "Cationic lipids enhance cellular uptake and activity of phosphorothioate antisense oligonucleotides" Mol. Pharmacol. (1992) 41(6): 1023-1033.
Bennett et al., "RNA targeting therapeutics: molecular mechanisms of antisense oligonucleotides as a therapeutic platform" Ann. Rev. Pharmacol. Toxicol. (2010) 50: 259-293.
Bharadwaj et al., "Annexin A2 heterotetramer: structure and function" Int J Mol Sci (2013) 14(3): 6259-6305.

(Continued)

*Primary Examiner* — Amy H Bowman
(74) *Attorney, Agent, or Firm* — McNeill Baur PLLC

(57) ABSTRACT

In certain embodiments, the present disclosure provides compounds and methods for increasing the antisense activity of an antisense compound in a cell. In certain embodiments, the present disclosure provides methods for identifying antisense compounds having high activity. In certain embodiments, the present disclosure provides methods for identifying antisense compounds that bind to enhancer or repressor proteins.

12 Claims, No Drawings
Specification includes a Sequence Listing.

(56) References Cited

OTHER PUBLICATIONS

Brown et al., "Effect of phosphorothioate modification of oligodeoxynucleotides on specific protein binding" J. Biol. Chem. (1994) 269(43): 26801-26805.
Conesa et al., "Sub1/PC4 a chromatin associated protein with multiple functions in transcription" RNA Biol. (2010) 7(3): 287-290.
Dias et al., "Antisense Oligonucleotides: Basic Concepts and Mechanisms" Mol. Cancer Ther. (2002) 1: 347-355.
Geary et al., Pharmacokinetic/Pharmacodynamic Properties of Phosphorothioate 2'-O-(2'Methoxyethyl)-Modified Antisense Oligonucleotides in Animals and Man. In: Crooke,ST (ed). *Antisense Drug Technology—Principles, Strategies, and Applications*. (2008) : 305-326.
Hartig et al., "Active nuclear import of single-stranded oligonucleotides and their complexes with non-karyophilic macromolecules" Biol Cell (1998) 90(5): 407-426.
International Search Report for PCT/US16/19165 dated May 19, 2016.
Jin et al., "Double-strand break repair by Ku70 requires heterodimerization with Ku80 and DNA binding functions" EMBO J (1997) 16(22): 6874-6885.
Juliano et al., "Cellular uptake and intracellular trafficking of antisense and siRNA oligonucleotides" Bioconjug. Chem. (2012) 23(2): 147-157.
Juliano et al., "Receptors, endocytosis, and trafficking: the biological basis of targeted delivery of antisense and siRNA oligonucleotides" J. Drug Target (2013) 21(1): 27-43.
Koller et al., "Mechanisms of single-stranded phosphorothioate modified antisense oligonucleotide accumulation in hepatocytes" Nucleic Acids Res. (2011) 39(11): 4795-4807.
Li et al., "Involvement of p54(nrb), a PSF partner protein, in DNA double-strand break repair and radioresistance" Nucleic Acids Res. (2009) 37(20): 6746-6753.
Liang et al., "Efficient and specific knockdown of small non-coding RNAs in mammalian cells and in mice" Nucleic Acids Res. (2011) 39(3): e13.
Liang et al., "Identification and characterization of intracellular proteins that bind oligonucleotides with phosphorothioate linkages" Nucleic Acids Res. (2015) 43(5): 2927-2945.
Liang et al., "TCP1 complex proteins interact with phosphorothioate oligonucleotides and can co-localize in oligonucleotide-induced nuclear bodies in mammalian cells" Nucleic Acids Res. (2014) 42(12): 7819-7832.
Lima et al., "Defining the factors that contribute to on-target specificity of antisense oligonucleotides" PLOS One (2014) 9(7): e101752.
Lorentz et al., "Nucleocytoplasmic shuttling: a novel in vivo property of antisense phosphorothioate oligodeoxynucleotides" Nucleic Acids Res. (2000) 28(2): 582-592.
Maggi et al., "Nucleophosmin serves as a rate-limiting nuclear export chaperone for the Mammalian ribosome" Mol Cell Biol (2008) 28(23): 7050-7065.
Marcusson et al., "Phosphorothioate oligodeoxyribonucleotides dissociate from cationic lipids before entering the nucleus" Nucleic Acids Res. (1998) 26(8): 2016-2023.
Morel et al., "Annexin A2 binding to endosomes and functions in endosomal transport are regulated by tyrosine 23 phosphorylation" J Biol Chem (2009) 284(3): 1604-1611.
Naeeni et al., "RNA chaperone activity of human La protein is mediated by variant RNA recognition motif" J Biol Chem (2012) 287(8): 5472-5482.
Okuwaki et al., "The structure and functions of NPM1/Nucleophsmin/B23, a multifunctional nucleolar acidic protein" J Biochem (2008) 143(4): 441-448.
Sasaki et al., "MENepsilon/beta noncoding RNAs are essential for structural integrity of nuclear paraspeckles" PNAS (2009) 106(8): 2525-2530.
Shen et al., "Phosphorothioate oligonucleotides can displace NEAT1 RNA and form nuclear paraspeckle-like structures" Nucleic Acids Res. (2014) 42(13): 8648-8662.
Song et al., "Oxidative stress induces nuclear loss of DNA repair proteins Ku70 and Ku80 and apoptosis in pancreatic acinar AR42J cells" J Biol Chem (2003) 278(38): 36676-36687.
Stein et al., "Efficient gene silencing by delivery of locked nucleic acid antisense oligonucleotides, unassisted by transfection reagents" Nucleic Acids Res. (2010) 38(1): e3.
Swayze et al., The Medicial Chemistry of Oligonucleotides. In: Crooke,ST (ed). *Antisense Drug Technology—Principles, Strategies, and Applications* 2nd edn. (2008) : 143-182.
Vickers et al., "Antisense Oligonucleotides Capable of Promoting Specific mRNA Reduction via Competing Rnase H1-Dependent and Independent Mechanisms" PLOS One (2014) 9: e108625.
Weidner et al., "Phosphorothioate oligonucleotides bind in a non sequence-specific manner to the nucleolar protein C23/nucleolin" FEBS Lett. (1995) 366: 146-150.
Wolin et al., "The La protein" Annu Rev Biochem (2002) 71: 375-403.
Wu et al., "Determination of the role of the human RNase H1 in the pharmacology of DNA-like antisense drugs" J. Biol. Chem. (2004) 279(17): 17181-17189.
Wu et al., "Human RNase H1 is associated with protein P32 and is involved in mitochondrial pre-rRNA processing" PLOS One (2013) 8(8): e71006.
Yu et al., "A new method for detecting sites of 2'-O-methylation in RNA molecules" RNA (1997) 3:324-331.
Yu et al., "Nucleophosmin is essential for ribosomal protein L5 nuclear export" Mol Cell Biol (2006) 26(10): 3798-3809.
Zelphati et al., "Mechanism of oligonucleotide release from cationic liposomes" PNAS (1996) 93(21): 11493-11498.

\* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucletide

<400> SEQUENCE: 1
ctgctagcct cuggatttga                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
ctgctagcct ctggatttga                                              20

<210> SEQ ID NO 3
<211> LENGTH: 28
<212> TYPE: RNA
<213> ORGANISM: Artificial sequence
<220> FEATURE:
<223> OTHER INFORMATION: Synthetic oligonucleotide

<400> SEQUENCE: 3
agcaguucuc aaauccagag gcuagcag                                     28

<210> SEQ ID NO 4
<211> LENGTH: 28
<212> TYPE: RNA
<213> ORGANISM: Artificial sequence
<220> FEATURE:
<223> OTHER INFORMATION: Synthetic oligonucleotide

<400> SEQUENCE: 4
agcaguucgu gauggguuug ucugcgcu                                     28

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gtcatcgtca tcctcatcat                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cagcaggcaa ctgtcgctga                                              20

<210> SEQ ID NO 7
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 7
ggcatatgca gataatgttc                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ttttggcaaa gtaatcgtcc                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
taaagtgata atctttgtcg                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
atccctttct tccgcatgtg                                              20
```

COMPOUNDS AND METHODS FOR INCREASING ANTISENSE ACTIVITY

SEQUENCE LISTING

The present application is being filed along with a Sequence Listing in electronic format. The Sequence Listing is provided as a file entitled CORE0133USASEQ_ST25.txt, created Aug. 22, 2017, which is 4 Kb in size. The information in the electronic format of the sequence listing is incorporated herein by reference in its entirety.

BACKGROUND

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. For another example, an antisense compound targeting ApoB, KYNAMRO™, has been approved by the U.S. Food and Drug Administration (FDA) as an adjunct treatment to lipid-lowering medications and diet to reduce low density lipoprotein-cholesterol (LDL-C), ApoB, total cholesterol (TC), and non-high density lipoprotein-cholesterol (non HDL-C) in patients with homozygous familial hypercholesterolemia (HoFH).

SUMMARY

In certain embodiments, the present disclosure provides methods of screening for the affinity between an antisense oligonucleotide and one or more antisense oligonucleotide binding protein. In certain embodiments, antisense oligonucleotide binding proteins include repressor proteins which inhibit antisense activity. In certain embodiments, antisense oligonucleotide binding proteins include repressor proteins which increase antisense activity. In certain embodiments, antisense oligonucleotides may be screened for affinity towards repressor and enhancer proteins. In certain embodiments, antisense oligonucleotides identified as having high affinity for enhancer proteins have more antisense activity than antisense oligonucleotides having low affinity for enhancer proteins. In certain embodiments, antisense oligonucleotides identified as having high affinity for repressor proteins have less antisense activity than antisense oligonucleotides having low affinity for repressor proteins. In certain embodiments, antisense oligonucleotides identified as having high affinity for repressor proteins have less antisense activity than antisense oligonucleotides having low affinity for repressor proteins. In certain embodiments, antisense oligonucleotides identified as having low affinity for enhancer proteins have less antisense activity than antisense oligonucleotides having high affinity for enhancer proteins.

In certain embodiments, the present disclosure provides a method for increasing the antisense activity of an antisense compound in a cell, comprising inhibiting the amount or activity of an antisense oligonucleotide binding protein in the cell and contacting the cell with the antisense compound.

In certain embodiments, the present disclosure provides a method of screening for antisense oligonucleotides that bind to at least one enhancer protein, comprising:

attaching a first antisense oligonucleotide to a solid support wherein the first antisense oligonucleotide binds to the enhancer protein;

contacting the first antisense oligonucleotide with the at least one enhancer protein; washing the solid support to remove enhancer protein that is not associated with the first antisense oligonucleotide;

contacting the enhancer protein bound to the first antisense oligonucleotide with a second antisense oligonucleotide;

collecting protein that is no longer associated with the first antisense oligonucleotide by eluting it from the solid support; and detecting the presence or amount of the at least one enhancer protein in the eluent.

In certain embodiments, the present disclosure provides a method of screening for antisense oligonucleotides that do not bind to or bind weakly to a ASO repressor protein, comprising:

attaching a first antisense oligonucleotide to a solid support wherein the first antisense oligonucleotide binds to the repressor protein;

contacting the first antisense oligonucleotide with the at least one repressor protein;

washing the solid support to remove protein that is not associated with the first antisense oligonucleotide;

contacting the repressor protein bound to the first antisense oligonucleotide with a second antisense oligonucleotide;

collecting protein that is no longer associated with the first antisense oligonucleotide by eluting it from the solid support; and determining the presence or absence of the at least one repressor protein in the eluent.

The present disclosure provides the following non-limiting numbered embodiments:

Embodiment 1: A method for increasing the antisense activity of an antisense compound in a cell, comprising: inhibiting the amount or activity of an antisense oligonucleotide binding protein in the cell; and contacting the cell with the antisense compound.

Embodiment 2: The method of embodiment 1, wherein the antisense oligonucleotide binding protein is a repressor protein.

Embodiment 3: The method of any of embodiments 1 or 2, wherein the antisense compound comprises an antisense oligonucleotide.

Embodiment 4: The method of any of embodiments 1-3, wherein the amount or activity of the protein is inhibited by inhibiting the amount or activity of the mRNA that codes for the protein.

Embodiment 5: The method of any of embodiments 1-4, wherein the amount or activity of the protein is inhibited by contacting the cell with an antisense compound targeting a nucleic acid that codes for the protein.

Embodiment 6: The method of any of embodiments 1-5, wherein the protein is selected from Ku70, Ku80, hnRNPK, P54nrb, PSF, and PSPC1.

Embodiment 7: The method of embodiment 6, wherein the protein is selected from Ku70 and Ku80.

Embodiment 8: The method of embodiment 6, wherein the protein is selected from hnRNPK, P54nrb, PSF, and PSPC1.

Embodiment 9: The method of any of embodiments 1-8, wherein the antisense compound comprises at least one phosphorothioate internucleoside linkage.

Embodiment 10: The method of embodiment 9, wherein the antisense compound comprises a plurality of phosphorothioate internucleoside linkages.

Embodiment 11: The method of embodiment 10, wherein all of the internucleoside linkages of the antisense compound are phosphorothioate internucleoside linkages.

Embodiment 12: The method of any of embodiments 1-11, wherein at least one nucleoside of the antisense compound comprises a modified nucleobase.

Embodiment 13: The method of embodiment 12, wherein at least one modified nucleobase is a 5-methylcytosine.

Embodiment 14: The method of embodiment 12, wherein at least one modified nucleobase is a hypoxanthine.

Embodiment 15: The method of any of embodiments 1-14, wherein at least one nucleoside of the antisense compound comprises a modified sugar.

Embodiment 16: The method of any of embodiments 1-16, wherein the modified sugar is a bicyclic sugar.

Embodiment 17: The method of embodiment 17, wherein the bicyclic sugar comprises a chemical bridge between the 2' and 4' position of the sugar, wherein the chemical bridge is selected from: 4'-CH2-O-2'; 4'-CH(CH3)-O-2'; 4'-(CH2)2-O-2'; and 4'-CH2-N(R)—O-2' wherein R is, independently, H, C1-C12 alkyl, or a protecting group.

Embodiment 18: The method of embodiment 15, wherein the modified sugar comprises a 2'-modification selected from 2'-fluoro, 2'OMe, and 2'-MOE.

Embodiment 19: The method of embodiment 15, wherein at least one modified sugar comprises a 2'-O-methoxyethyl group.

Embodiment 20: The method of embodiment 19, wherein each modified sugar comprises a 2'-O-methoxyethyl group.

Embodiment 21: The method of any of embodiments 1-15 or 17-21, wherein the antisense compound comprises modifications at the 2' position of every nucleoside.

Embodiment 22: The method of any of embodiments 1-20, wherein the antisense compound comprises a gapmer.

Embodiment 23: The method of any of embodiments 1-22, wherein the antisense compound targets a microRNA.

Embodiment 24: The method of any of embodiments 1-23, wherein the antisense compound comprises at least one conjugate.

Embodiment 25: A method of screening for antisense oligonucleotides that bind to at least one enhancer protein, comprising:
  attaching a first antisense oligonucleotide to a solid support wherein the first antisense oligonucleotide binds to the enhancer protein;
  contacting the first antisense oligonucleotide with the at least one enhancer protein;
  washing the solid support to remove enhancer protein that is not associated with the first antisense oligonucleotide;
  contacting the enhancer protein bound to the first antisense oligonucleotide with a second antisense oligonucleotide;
  collecting protein that is no longer associated with the first antisense oligonucleotide by eluting it from the solid support; and
  detecting the presence or amount of the at least one enhancer protein in the eluent.

Embodiment 26: The method of embodiment 25, wherein the at least one enhancer protein is selected from La/SSB, NPM1, Annexin A2, PC4/SUB1, TCP1-alpha, TCP1-beta, TCP1-epsilon, and VARS.

Embodiment 27: The method of embodiment 26, wherein the at least one enhancer protein is selected from NPM1 and La/SSB.

Embodiment 28: The method of embodiment 26, wherein the at least one enhancer protein is selected from Annexin A2, PC4/SUB1, TCP1-alpha, TCP1-beta, TCP1-epsilon, and VARS.

Embodiment 29: The method of any of embodiments 25-28, wherein the presence or amount of two enhancer proteins is detected.

Embodiment 30: The method of any of embodiments 14, 15, or 17, wherein the presence or amount of three enhancer proteins is detected.

Embodiment 31: The method of any of embodiments 25, 26, or 28, wherein the presence or amount of four enhancer proteins is detected.

Embodiment 32: The method of any of embodiments 25-31, wherein the first oligonucleotide is contacted with cell lysate containing the at least one enhancer protein.

Embodiment 33: The method of any of embodiments 25-31, wherein the at least one enhancer protein is purified.

Embodiment 34: The method of any of embodiments 25-33, wherein the antisense oligonucleotide comprises at least one modified sugar.

Embodiment 35: The method of embodiment 34, wherein the at least one modified sugar is a bicyclic sugar.

Embodiment 36: The method of embodiment 35, wherein the bicyclic sugar comprises a chemical bridge between the 2' and 4' position of the sugar, wherein the chemical bridge is selected from: 4'-CH2-O-2'; 4'-CH(CH3)-O-2'; 4'-(CH2)2-O-2'; and 4'-CH2-N(R)—O-2' wherein R is, independently, H, C1-C12 alkyl, or a protecting group.

Embodiment 37: The method of any of embodiments 34-36, wherein the antisense oligonucleotide comprises at least one modified sugar having a 2'-modification.

Embodiment 38: The method of embodiment 37, wherein the at least one 2'-modification is selected from 2'-fluoro, 2'OMe, and 2'-MOE.

Embodiment 39: The method of embodiment 37, wherein the at least one 2'-modification is 2'-MOE.

Embodiment 40: The method of any of embodiments 25-39, wherein the antisense oligonucleotide is a gapmer.

Embodiment 41: The method of any of embodiments 25-39, wherein the antisense compound comprises modifications at the 2' position of every nucleoside.

Embodiment 42: The method of any of embodiments 25-39, wherein the antisense oligonucleotide comprises a conjugate.

Embodiment 43: A method of screening for antisense oligonucleotides that do not bind to or bind weakly to a ASO repressor protein, comprising:
  attaching a first antisense oligonucleotide to a solid support wherein the first antisense oligonucleotide binds to the repressor protein;

contacting the first antisense oligonucleotide with the at least one repressor protein;

washing the solid support to remove protein that is not associated with the first antisense oligonucleotide;

contacting the repressor protein bound to the first antisense oligonucleotide with a second antisense oligonucleotide;

collecting protein that is no longer associated with the first antisense oligonucleotide by eluting it from the solid support; and determining the presence or absence of the at least one repressor protein in the eluent.

Embodiment 44: The method of embodiment 43, wherein the at least one repressor protein is selected from Ku70, Ku80, hnRNPK, P54nrb, PSF, and PSPC1.

Embodiment 45: The method of embodiment 44, wherein the at least one repressor protein is selected from Ku70 and Ku80.

Embodiment 46: The method of embodiment 44, wherein the at least one repressor protein is selected from hnRNPK, P54nrb, PSF, and PSPC1.

Embodiment 47: The method of embodiment 44, wherein the at least one repressor protein is a paraspeckle protein.

Embodiment 48: The method of any of embodiments 43-47, wherein the presence or amount of two repressor proteins is detected.

Embodiment 49: The method of any of embodiments 43, 44, or 46-47, wherein the presence or amount of three repressor proteins is detected.

Embodiment 50: The method of any of embodiments 43, 44, or 46-47, wherein the presence or amount of four repressor proteins is detected.

Embodiment 51: The method of any of embodiments 43-50, wherein the first oligonucleotide is contacted with cell lysate containing the at least one repressor protein.

Embodiment 52: The method of any of embodiments 43-51, wherein the at least one repressor protein is purified.

Embodiment 53: The method of any of embodiments 43-52, wherein the antisense oligonucleotide comprises at least one modified sugar.

Embodiment 54: The method of embodiment 53, wherein the at least one modified sugar is a bicyclic sugar.

Embodiment 55: The method of embodiment 54, wherein the bicyclic sugar comprises a chemical bridge between the 2' and 4' position of the sugar, wherein the chemical bridge is selected from: 4'-CH2-O-2'; 4'-CH(CH3)-O-2'; 4'-(CH2)2-O-2'; and 4'-CH2-N(R)—O-2' wherein R is, independently, H, C1-C12 alkyl, or a protecting group.

Embodiment 56: The method of any of embodiments 42-55, wherein the antisense oligonucleotide comprises at least one modified sugar having a 2'-modification.

Embodiment 57: The method of embodiment 56, wherein the at least one 2'-modification is selected from 2'-fluoro, 2'OMe, and 2'-MOE.

Embodiment 58: The method of embodiment 56, wherein the at least one 2'-modification is 2'-MOE.

Embodiment 59: The method of any of embodiments 43-58, wherein the antisense oligonucleotide is a gapmer.

Embodiment 60: The method of any of embodiments 43-58, wherein the antisense compound comprises modifications at the 2' position of every nucleoside.

Embodiment 61: The method of any of embodiments 43-60, wherein the antisense compound comprises a conjugate.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless Otherwise Indicated, the Following Terms have the Following Meanings:

As used herein, "antisense oligonucleotide binding protein" means any protein that binds with an antisense oligonucleotide. In certain embodiments, an antisense oligonucleotide binding protein is an enhancer protein. In certain embodiments, an antisense oligonucleotide binding protein is a repressor protein.

As used herein, "enhancer protein" means protein that binds to an antisense oligonucleotide, and antisense activity of an antisense oligonucleotide is decreased when expression or activity of the enhancer protein is inhibited.

As used herein, "repressor protein" means protein that binds to an antisense oligonucleotide, and antisense activity of an antisense oligonucleotide is increased when expression or activity of the repressor protein is inhibited.

As used herein, "paraspeckle protein" means any protein that is associated with or localized in a ribonucleoprotein paraspeckle.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligonucleotide which is capable of hybridizing to a complementary oligonucleotide. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH)CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage. Examples of modified oligonucleotides include single-stranded and double-stranded compounds, such as, antisense compounds, siRNAs, shRNAs, ssRNAs, and occupancy-based compounds.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, the sub-structures are nucleotides or nucleosides. In certain embodiments, an oligomeric compound comprises an oligonucleotide. In certain embodiments, an oligomeric compound consists of an oligonucleotide. In certain embodiments, an oligomeric compound consists of an antisense compound.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate group" means an atom or group of atoms bound to an oligonucleotide or oligomeric compound. In general, conjugate groups modify one or more properties of the oligonucleotide or oligomeric compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), translation, and post-translational modification.

As used herein, "translation" means the process in which a polypeptide (e.g. a protein) is translated from an mRNA. In certain embodiments, an increase in translation means an increase in the number of polypeptide (e.g. a protein) molecules that are made per copy of mRNA that encodes said polypeptide.

As used herein, "target nucleic acid" means a nucleic acid molecule to which an antisense compound is intended to hybridize.

As used herein, "mRNA" means an RNA molecule that encodes a protein.

As used herein, "pre-mRNA" means an RNA transcript that has not been fully processed into mRNA. Pre-RNA includes one or more intron.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense compound specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)),imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC)(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$, is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula -C(O)-X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond.

An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

Certain Modified Oligonucleotides

In certain embodiments, the present invention provides antisense compounds. In certain embodiments, antisense compounds comprise a modified oligonucleotide. In certain embodiments, such antisense compounds comprise modified oligonucleotides and optionally one or more conjugate and/or terminal groups. In certain embodiments, an antisense compound consists of a modified oligonucleotide. In certain embodiments, modified oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are antisense compounds comprising or consisting of oligonuleotides comprising at least one modified nucleoside. Such modified nucleosides comprise a modified sugar moeity, a modified nucleobase, or both a modifed sugar moiety and a modified nucleobase.

i. Certain Sugar Moieties

In certain embodiments, antisense compounds of the invention comprise one or more modifed nucleosides comprising a modifed sugar moiety. Such antisense compounds comprising one or more sugar-modified nucleosides may have desirable properties, such as enhanced nuclease stability or increased binding affinity with a target nucleic acid relative to antisense compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to:, 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'- substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'- substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'- substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$—(CH$_2$)$_2$N(CH$_3$)$_2$, and O—CH$_2$—C(=O)—N(H)CH$_3$.

In certain embodiments, a 2'- substituted nucleoside comprises a sugar moiety comprising a 2'-substituent group selected from F, O—CH$_3$, and OCH$_2$CH$_2$OCH$_3$.

Certain modfed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, [—C(R$_a$)(R$_b$)]$_n$—O—, —C(R$_a$R$_b$)—N(R)—O— or, —C(R$_a$R$_b$)—O—N(R)—; 4'- CH$_2$-2 ', 4'-(CH$_2$)$_2$-2', 4'-(CH$_2$)$_3$-2',4'-(CH$_2$)—O-2' (LNA); 4'-(CH$_2$)—S-2'; 4'-(CH$_2$)$_2$—O-2' (ENA); 4'-CH)CH$_3$)—O-2' (cEt) and 4'-CH(CH$_2$OCH$_3$)—O-2$^1$, and analogs thereof (see, e.g., U.S. Pat. No. 7,399,845, issued on Jul. 15, 2008); 4'-C(CH$_3$)(CH$_3$)—O-2'and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from [C(R$_a$)(R$_b$)]$_n$—, —C(R$_a$)=C(R$_b$)—, —C(R$_a$)=N—, —C(=NR$_a$)—, —C(=O)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) α-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH)CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (M) 4'-CH$_2$—O—CH$_2$-2' as depicted below.

(A)

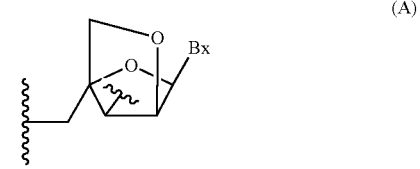

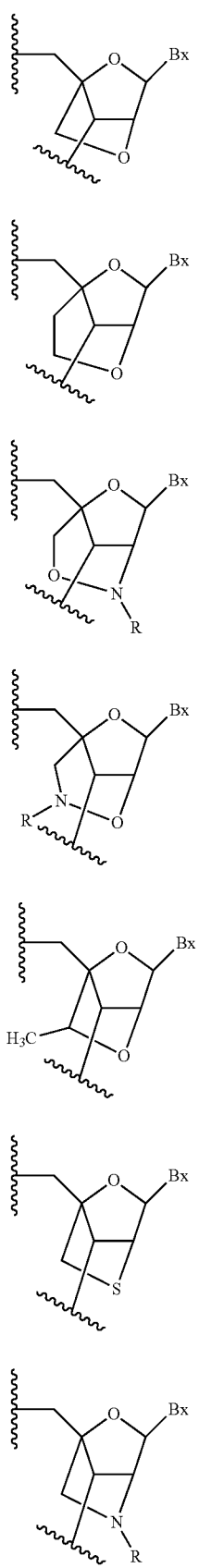
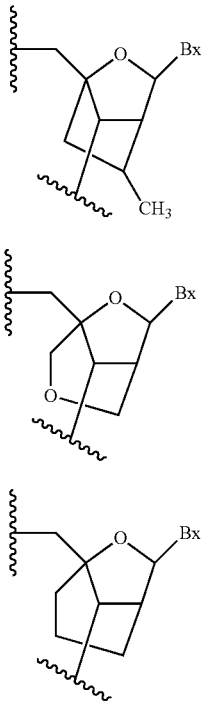

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the (β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2¹-position (see,e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

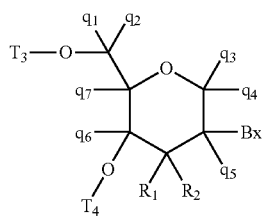

VII wherein independently for each of said at least one tetrahydropyran nucleoside analog of Formula VII:
Bx is a nucleobase moiety;
$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)$ $NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

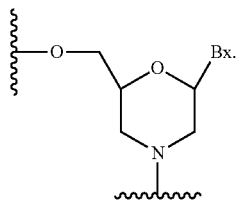

In certain embodiments, morpholinos may be modified, for example by adding or altering various substituent groups from the above morpholino structure. Such sugar surrogates are refered to herein as "modifed morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in United States Patent No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y.S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y.S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

c. Certain Motifs

In certain embodiments, the invention provides modified oligocucleotides. In certain embodiments, modified oligonucleotides comprise one or more modified sugars. In certain embodiments, modified oligonucleotides comprise one or more modified nucleobases. In certain embodiments, modified oligonucleotides comprise one or more modified internucleoside linkages. In certain embodiments, the modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, a modifed oligonucleotide may be described by its sugar modification motif, internucleoside linkage motif and/or nucleobase modification motif (as used herein, nucleobase modification motif describes the chemical modifications to the nucleobases independent of the sequence of nucleobases).

In certain embodiments, every sugar moiety of the modified oligonucleotides of the present invention is modified. In certain embodiments, modified oligonucleotides include one or more unmodified sugar moiety.

d. Certain Overall Lengths

In certain embodiments, the present invention provides modified oligonucleotidesof any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides modified oligonucleotides which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17,11to 18,11to 19,11to 20,11to 21, 11 to 22,11to 23,11to 24,11to 25,11to 26, 11 to 27,11to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another.

f. Certain Conjugate Groups

In certain embodiments, the oligonucleotides or oligomeric compounds as provided herein are modified by covalent attachment of one or more conjugate groups. In general, conjugate groups modify one or more properties of the attached oligonucleotide or oligomeric compound including but not limited to pharmacodynamics, pharmacokinetics, stability, binding, absorption, cellular distribution, cellular uptake, charge and clearance. As used herein, "conjugate group" means a radical group comprising a group of atoms that are attached to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligonucleotide or oligomeric compound. In certain embodiments, conjugate groups include a cleavable moiety that covalently links the conjugate group to an oligonucleotide or oligomeric compound. In certain embodiments, conjugate groups include a conjugate linker and a cleavable moiety to covalently link the conjugate group to an oligonucleotide or oligomeric compound. In certain embodiments, a conjugate group has the general formula:

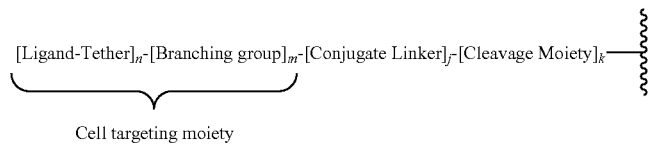

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5$^1$-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3 -O-[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3, 4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry,* 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

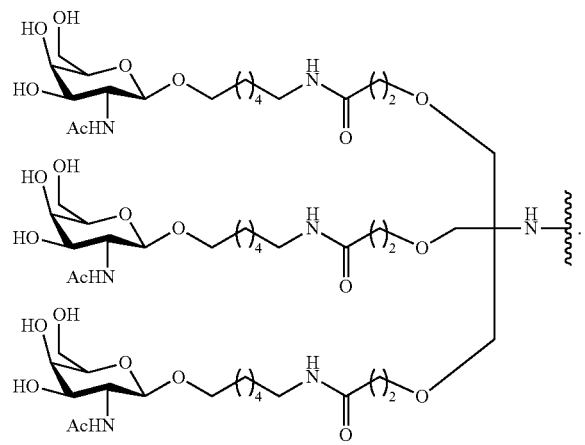

In certain embodiments, conjugate groups are provided wherein the cell-targeting moiety has the formula:

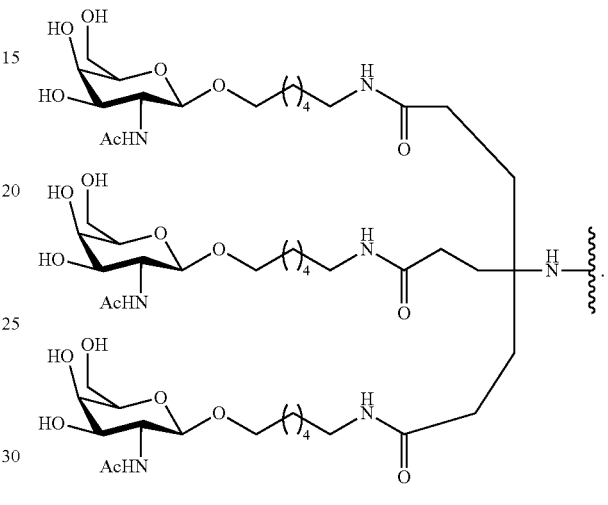

In certain embodiments, conjugate groups are provided wherein the cell-targeting moiety has the formula:

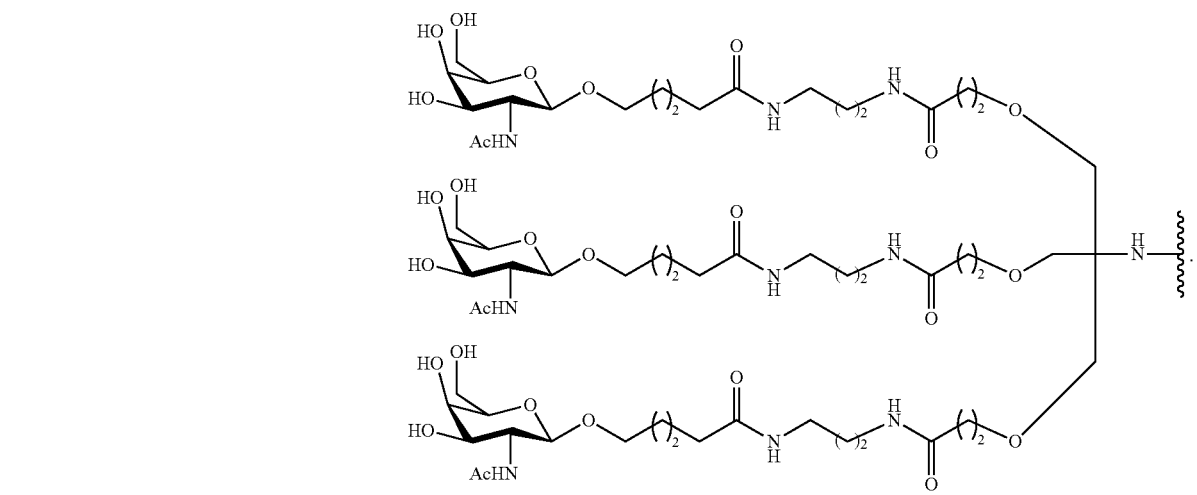

In certain embodiments, conjugate groups have the formula:

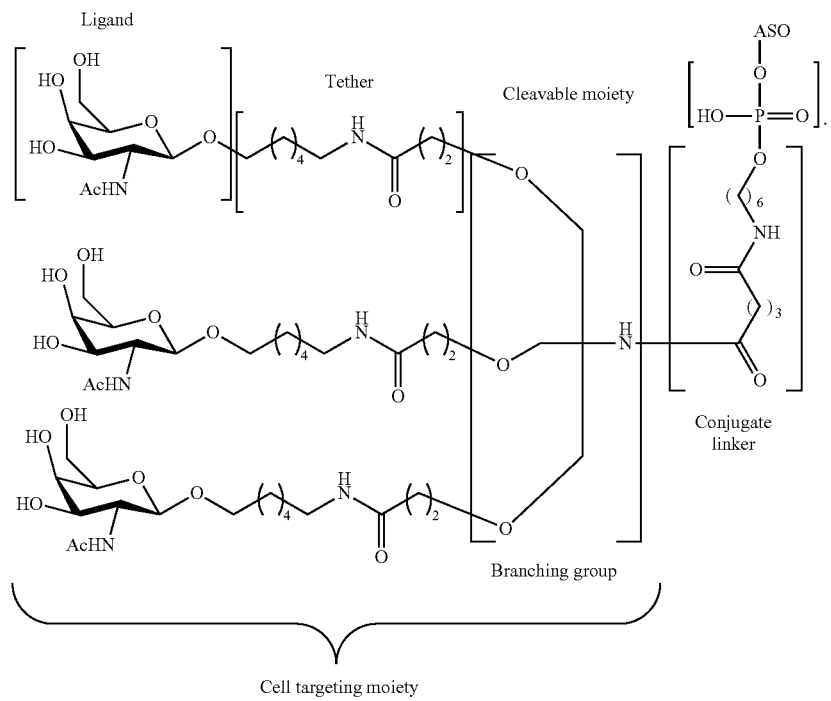

Representative United States patents, United States patent application publications, and international patent application publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetyl-galactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-

237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

Some nonlimiting examples of conjugate linkers include pyrrolidine, 8-amino-3,6-dioxaoctanoic acid (ADO), succinimidyl 4-(N-maleimidomethyl) cyclohexane-l-carboxylate (SMCC) and 6-aminohexanoic acid (AHEX or AHA). Other connugate linkers include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

B. Antisense Compounds

In certain embodiments, modified oligonucleotides provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

The present disclosure identifies a number of antisense oligonucleotide binding proteins. In certain embodiments, one or more antisense oligonucleotide binding proteins may alter the amount or acticity of any given antisense oligonucleotide. For example, in certain embodiments, an antisense oligonucleotide binding protein may be a repressor protein, in which case the binding of the repressor protein to a given antisense oligonucleotide would thereby decrease the activity of the antisense oligonucleotide. In certain embodiments, an antisense oligonucleotide binding protein may be an enhancer protein, in which case the binding of the enhancer protein to a given antisense oligonucleotide would thereby increase the activity of the antisense oligonucleotide.

In certain embodiments, an antisense oligonucleotide may possess a number of modifications, for example an antisense oligonucleotide may have a plurality of 2'-modifications or bicycic modifications, and these modifications change the affinity of a given antisense oligonucleotide for certain repressor proteins and/or enhancer proteins. In certain embodiments, an antisense oligonucleotide may possess a given nucleobase sequence, and the nucleobase sequence may change the affinity of a given antisense oligonucleotide for certain repressor proteins and/or enhancer proteins.

In certain emobdiments, an antisense oligonucleotide may be screened for its affinity towards repressor proteins and enhancer proteins. In certain embodiments, antisense oligonucleotides that have greater affinity for enhancer proteins may be identified as particularly active. In certain embodiments, antisense oligonucleotides that have low affinity for repressor proteins may be identified as particularly active. In certain embodiments, antisense oligonucleotides that have greater affinity for repressor proteins may be identified as having reduced activity as compared to an antisense oligonucleotide that does not have strong affinity for one or more repressor proteins. In certain embodiments, antisense oligonucleotides that have low affinity for enhancer proteins may be identified as having reduced activity as compared to an antisense oligonucleotide that does not have low affinity for one or more enhancer proteins. In certain emobdiments, an antisense oligonucleotide may be screened for its affinity towards repressor proteins and enhancer proteins. For example, an antisense oligonucleotide may be screened for its high affinity towards enhacner proteins and its low affinity for repressor proteins. In certain embodiments active antisense oligonucleotides may be identified by screening antisense oligonucleotides and identifying antisense oligonucleotides that possess high affinity towards enhacner proteins and low affinity for repressor proteins.

In certan embodiments, enhancer proteins bind to antisense oligonucleotides and increase the antisense activity of the antisense oligonucleotide. In certan embodiments, enhancer proteins preferentially alter the subcellular localization of antisense oligonucleotides. For example, in certain embodiments, enhancer protiens facilitate the release of antisense oligonucleotides from the endocytic pathway.

In certain embodiments, an enhancer protein is selected from La/SSB, NPMI, Annexin A2, PC4/SUB1, TCP1-alpha, TCP1-beta, TCP1-epsilon, and VARS. In certain embodiments, an enhancer protein is La/SSB. In certain embodiments, an enhancer protein is NPMI. In certain embodiments, an enhancer protein is La/SSB. In certain embodiments, an enhancer protein is Annexin A2. In certain embodiments, an enhancer protein is PC4/SUB1. In certain embodiments, an enhancer protein is TCP1-alpha. In certain embodiments, an enhancer protein is TCP1-beta. In certain embodiments, an enhancer protein is TCP1-epsilon. In certain embodiments, an enhancer protein is VARS.

In certan embodiments, repressor proteins bind to antisense oligonucleotides and decrease the antisense activity of the antisense oligonucleotide. In certan embodiments, repressor proteins compete with RNase H1 for binding with the antisense oligonucleotide, thereby resulting in decreased antisense activity.

In certain embodiments, a repressor protein is selected from Ku70, Ku80, hnRNPK, P54nrb, PSF, and PSPC1. In certain embodiments, a repressor protein is Ku70. In certain embodiments, a repressor protein is Ku80. In certain embodiments, a repressor protein is hnRNPK. In certain embodiments, a repressor protein is P54nrb. In certain embodiments, a repressor protein is PSF. In certain embodiments, a repressor protein is PSPC1.

C. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives).

In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

D. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments, the targeted tissue is striatal tissue. In certain embodiments, decreasing EC50 is desirable because it reduces the dose required to achieve a pharmacological result in a patient in need thereof.

In certain embodiments, an antisense compound is delivered by injection or infusion once every month, every two months, every 90 days, every 3 months, every 6 months, twice a year or once a year.

E. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^m$CGAUCG," wherein $^m$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Identification of Proteins that Specifically Associate with PS-ASOs in the Context of a Duplex An affinity selection method was used to identify cellular proteins that associate with phosphorothioate antisense oligonucletides (PS-ASOs). The PS-ASO used to capture the proteins was Isis No. 451104 (CTGCTAGCCTCUGGATTTGA, SEQ ID NO: 1) or Isis No. 386652 (CTGCTAGCCTCTGGATTTGA, SEQ ID NO: 2). Isis Numbers 451104 and 386652 are biotinylated 5-10-5 gapmers, in which each nucleotide in the wings is 2'-O-methoxyethyl (MOE) modified and each nucleotide in the gap is 2'-deoxy. All cytosines are 5-methylcytosines, the uracil is a 5-iodouracil, and all internucleoside linkages are phosphorothioate (PS). The 5'-ends are biotinylated via a tetraethyleneglycol linker. The PS-ASO used to elute the proteins bound to the capture PS-ASO was Isis No. 116847 (CTGCTAGCCTCTGGATTTGA, SEQ ID NO: 2), which is identical to Isis No. 386652 except that it contains a 5'-OH instead of a linker and biotin.

50 to 100 µL of neutravidin beads were incubated with 50 to 100 µL of 200 µM of a capture PS-ASO at 4° C. for 2 hrs in W-100 buffer (50 mM Tris pH 7.5, 100 mM KCl, 5 mM EDTA, 0.1% NP-40, 0.05% SDS), and blocked for 30 minutess with block buffer (10 mg/ml BSA, 1.2 mg/ml Glycogen, and 0.2 mg/ml tRNA in W-100). After washing 3 times with W-100, the ASO-coated beads were incubated at 4° C. for 3 hours with 300 to 3,000 µg HeLa cell extracts prepared in buffer A [25 mM Tris-HCl pH 8.0, 5 mM MgCl$_2$, 150 mM KCl, 10% glycerol, 0.5 mM PMSF, 5 mM β-mercaptoethanol, and one tablet of Protease Inhibitor Cocktail/50 mL (Roche)]. After washing 3 times with 500 µL wash buffer containing 200 mM KCl (W-200), beads were transferred to a 1 mL column and washed 7 times with W-200. Bound proteins were eluted by incubation with 100 to 200 µL of 50 µM Isis No. 116847 in W-100 at room temperature for 30 minutes and are referred to as sample #1.

Some of the eluted material (sample #1) was diluted with 100 µL W-100 in preparation for another series of capture and elution steps designed to identify proteins that bind to PS-ASOs in the context of a duplex and to eliminate proteins that do not specifically associate with PS-ASOs. 30 µL of neutravidin beads were first incubated with 30 µL of 200 µM biotinylated phosphodiester (PO) oligonucleotides complementary to Isis No. 116847 (AGCAGUUCUCAAAUCCAGAGGCUAGCAG, XL180, SEQ ID NO: 3) or non-complementary to Isis No. 116847 (AGCAGUUCGUGAUGGGUUUGUCUGCGCU, XL181, SEQ ID NO: 4). XL180 and 181 are biotinylated at the 5'end, and the first seven nucleotides of each oligonucleotide are unmodified ribonucleotides that constitute an RNaseI cleavage sequence. The remaining nucleotides are 2'-O-methyl modified, and all internucleoside linkages of each oligonucleotide are phosphodiester. The neutravidin beads bound to XL180 or XL181 were then incubated with the diluted sample #1. The neutravidin beads and associated oligonucleotide—protein complexes were washed 7 times with W-200, then treated with 100 µL TE buffer containing 5 units/µL RNaseI for 30 minutes at 30° C. The proteins eluted from XL180 (sample #2) and from XL181 (sample #3) were separately ethanol precipitated and analyzed via 4-12% PAGE. Sliver-staining was carried out using ProteoSilver™ Plus Silver Stain Kit (Sigma) according to manufacturer's instructions. The identities of the eluted proteins were determined by mass spectrometry. Proteins in sample #2 were identified as specifically associating with PS-ASOs in the context of a duplex, and proteins in sample #3 were identified as non-specifically associating with both PS-ASOs and PO-ASOs. Proteins identified as specifically associating with PS-ASOs by this method were confirmed by western blot and included Ku80, Ku70, PC4 (Sub1), ATAD3A, PSF, RNaseH1, VARS, TCP1-alpha, TCP1-beta, TCP1-epsilon, La (SSB), NPM1, ANXA2, NCL1, KCTD12, ACTB, and paraspeckle proteins P54nrb, PSPC1, and hnRNPK. Of these proteins, Ku80, Ku70, PC4, ATAD3A, P54nrb, PSF, RNaseHl, VARS, and TCP1-beta were identified in both samples #1 and #2, indicating that they bind both single-stranded PS-ASOs and PS-ASOs in the context of a duplex.

Example 2

Increased NCL1 PS-ASO Activity Following Reduction of Paraspeckle Protein Expression In order to test the possibility that the association of PS-ASOs with paraspeckle proteins affects the activity of PS-ASOs in cells, the activity of a PS-ASO targeting NCL1 was analyzed following reduction of paraspeckle protein expression. HeLa cells were plated in 6-well dishes and grown to 70% confluency, then transfected with 3-5 nM siRNA targeting P54nrb or one non-paraspeckle protein that associates with PS-ASOs, LRPPRC, using Lipofectamine RNAiMax (Life Technologies) at a 6 µg/mL final concentration. The siRNAs were purchased from Life Technologies, catalog numbers s9612 or s9614 (P54nrb) and HSS115403 (LRPPRC). 20 hours after siRNA transfection, the cells were transfected with Isis No. 110074, a full PS, 5-10-5 MOE gapmer with 5-methyl cytosines targeted to NCL1 (GTCATCGTCATCCTCATCAT, SEQ ID NO: 5) using Lipofectamine 2000 (Life Technologies) at 4 µg/mL final concentration. Cells were harvested for RNA extraction 4 hours after transfection with Isis No. 110074, and NCL1 mRNA levels were analyzed via RT-PCR. Results are shown in Table 1 as percent RNA expression relative to cells that received no ASO treatment. "UTC" means untransfected control cells that were not transfected with siRNA (but may have been transfected with Isis No. 110074). As shown in Table 1, reduction of paraspeckle protein P54nrb expression prior to PS-ASO treatment resulted in greater PS-ASO activity than that achieved with treatment of the PS-ASO alone or the activity achieved following reduction of control protein LRPPRC expression. Thus, P54nrb was identified as a repressor protein of PS-ASO activity.

TABLE 1

NCL1 mRNA Expression

| Isis No. 110074 Concentration (nM) | siRNA Target | NCL1 mRNA (%) |
|---|---|---|
| 0 | UTC | 100.00 |
| 0 | P54nrb | 100.00 |
| 0 | LRPPRC | 100.00 |
| 1.5625 | UTC | 82.63 |
| 1.5625 | P54nrb | 72.65 |
| 1.5625 | LRPPRC | 82.25 |
| 3.125 | UTC | 72.93 |
| 3.125 | P54nrb | 55.77 |
| 3.125 | LRPPRC | 72.61 |
| 6.25 | UTC | 60.11 |
| 6.25 | P54nrb | 44.88 |
| 6.25 | LRPPRC | 56.13 |
| 12.5 | UTC | 31.04 |
| 12.5 | P54nrb | 29.91 |
| 12.5 | LRPPRC | 33.96 |
| 25 | UTC | 18.61 |
| 25 | P54nrb | 16.93 |
| 25 | LRPPRC | 24.50 |

Example 3

Increased NCL1 PS-ASO Activity Following Reduction of PS-ASO Associating Protein Expression In order to test the possibility that additional PS-ASO associating proteins affect the activity of PS-ASOs in cells, the activity of a PS-ASO targeting NCL1 was analyzed following reduction of expression of Ku70 or Ku80. HeLa cells were plated and treated as described in Example 2, except siRNA targeting Ku70 (cat. #2547 or 144693, Life Technologies) or Ku80 (cat. #139860 or 248391, Life Technologies) was used instead of siRNA targeting P54nrb. The cells were reseeded in 6 or 96 well plates at 50% confluency 8 to 24 hours after the siRNA transfection, incubated overnight, then transfected with Isis No. 110074. Cells were harvested, and mRNA was analyzed as described in Example 2. Results are shown in Table 2 as percent RNA expression relative to cells that received no ASO treatment. "UTC" means untransfected control cells that were not transfected with siRNA (but may have been transfected with Isis No. 110074). As shown in Table 2, reduction of Ku70 and Ku80 expression prior to PS-ASO treatment resulted in greater PS-ASO activity than that achieved with treatment of the PS-ASO alone or the activity achieved following reduction of LRPPRC expression. Thus, Ku70 and Ku80 were identified as repressor proteins of PS-ASO activity.

TABLE 2

NCL1 mRNA Expression

| Isis No. 110074 Concentration (nM) | siRNA Target | NCL1 mRNA (%) |
|---|---|---|
| 0 | UTC | 100.00 |
| 0 | Ku70 | 100.00 |
| 0 | Ku80 | 100.00 |
| 0 | LRPPRC | 100.00 |
| 1.9 | UTC | 58.04 |
| 1.9 | Ku70 | 51.55 |
| 1.9 | Ku80 | 49.86 |
| 1.9 | LRPPRC | 58.20 |
| 3.75 | UTC | 49.40 |
| 3.75 | Ku70 | 32.87 |
| 3.75 | Ku80 | 37.04 |
| 3.75 | LRPPRC | 50.75 |
| 7.5 | UTC | 34.81 |
| 7.5 | Ku70 | 23.31 |
| 7.5 | Ku80 | 20.02 |
| 7.5 | LRPPRC | 32.11 |
| 15 | UTC | 18.56 |
| 15 | Ku70 | 9.94 |
| 15 | Ku80 | 13.50 |
| 15 | LRPPRC | 15.65 |
| 30 | UTC | 14.48 |
| 30 | Ku70 | 8.55 |
| 30 | Ku80 | 7.61 |
| 30 | LRPPRC | 11.14 |

Example 4

Increased U16 PS-ASO Activity Following Reduction of Paraspeckle Protein Expression HeLa cells were plated in six-well dishes and treated with siRNA targeting P54nrb, as described in Example 2. To test the activity of another PS-ASO when paraspeckle protein expression is reduced, the cells were transfected with Isis No. 462026, a full PS, 5-10-5 2'-MOE gapmer with 5-methylcytosines (CAGCAGGCAACTGTCGCTGA, SEQ ID NO: 6) targeted to U16 snoRNA. The resulting levels of U16 snoRNA were analyzed via RT-PCR. Results are shown in Table 3 as percent RNA expression relative to cells that received no ASO treatment. "UTC" means untransfected control that was not transfected with siRNA (but may have been transfected with Isis No. 462026). As shown in Table 3, reduction of paraspeckle protein P54nrb expression prior to U16 PS-ASO treatment resulted in greater PS-ASO activity than that achieved with treatment of the PS-ASO alone.

TABLE 3

U16 snoRNA Expression

| Isis No. 462026 Concentration (nM) | siRNA Target | U16 snoRNA (%) |
|---|---|---|
| 0 | UTC | 100.00 |
| 0 | P54nrb | 100.00 |

TABLE 3-continued

U16 snoRNA Expression

| Isis No. 462026 Concentration (nM) | siRNA Target | U16 snoRNA (%) |
|---|---|---|
| 1.875 | UTC | 68.59 |
| 1.875 | P54nrb | 64.14 |
| 3.75 | UTC | 54.58 |
| 3.75 | P54nrb | 30.66 |
| 7.5 | UTC | 34.92 |
| 7.5 | P54nrb | 24.66 |
| 15 | UTC | 31.32 |
| 15 | P54nrb | 22.98 |
| 30 | UTC | 29.52 |
| 30 | P54nrb | 26.17 |

Example 5

Increased Malat1 PS-ASO Activity Following Reduction of Paraspeckle Protein Expression HeLa cells were plated in six-well dishes and treated with siRNA targeting P54nrb, PSPC1 (cat. #s30594, Life Technologies), or hnRNPK (cat. #s6737, Life Technologies), as described in Example 2. To test the activity of a PS-ASO targeting a long non-coding RNA when paraspeckle protein expression is reduced, the cells were transfected with Isis No. 395254, a full PS, 5-10-5 2'-MOE gapmer with 5-methylcytosines (GGCATATGCAGATAATGTTC, SEQ ID NO: 7) targeted to Malat1 mRNA. The resulting levels of Malat1 mRNA were analyzed via RT-PCR. Results are shown in Table 4 as percent RNA expression relative to cells that received no ASO treatment. "UTC" means untransfected control that was not transfected with siRNA (but may have been transfected with Isis No. 395254). As shown in Table 4, reduction of any of three different paraspeckle proteins prior to PS-ASO treatment resulted in greater Malat1 PS-ASO activity than that achieved with treatment of the PS-ASO alone.

TABLE 4

Malat1 mRNA Expression

| Isis No. 395254 Concentration (nM) | siRNA Target | Malat1 mRNA (%) |
|---|---|---|
| 0 | UTC | 100.00 |
| 0 | P54nrb | 100.00 |
| 0 | PSPC1 | 100.00 |
| 0 | hnRNPK | 100.00 |
| 0.625 | UTC | 85.78 |
| 0.625 | P54nrb | 60.79 |
| 0.625 | PSPC1 | 60.16 |
| 0.625 | hnRNPK | 61.00 |
| 1.25 | UTC | 74.84 |
| 1.25 | P54nrb | 59.35 |
| 1.25 | PSPC1 | 52.68 |
| 1.25 | hnRNPK | 48.17 |
| 2.5 | UTC | 64.61 |
| 2.5 | P54nrb | 46.23 |
| 2.5 | PSPC1 | 37.48 |
| 2.5 | hnRNPK | 44.05 |
| 5 | UTC | 55.72 |
| 5 | P54nrb | 38.37 |
| 5 | PSPC1 | 32.18 |
| 5 | hnRNPK | 30.56 |
| 10 | UTC | 53.62 |
| 10 | P54nrb | 37.51 |
| 10 | PSPC1 | 24.88 |
| 10 | hnRNPK | 24.41 |

Example 6

Increased PTEN PS-ASO Activity Following Reduction of Paraspeckle Protein Expression HeLa cells were plated in six-well dishes and treated with siRNA targeting P54nrb, as described in Example 2. To test the activity of another PS-ASO when paraspeckle protein expression is reduced, the cells were transfected with Isis No. 582801, a full PS, 5-10-5 2'-cEt gapmer with 5-methylcytosines (CTGCTAGCCTCTGGATTTGA, SEQ ID NO: 2) targeted to PTEN mRNA. The resulting levels of PTEN mRNA were analyzed via RT-PCR. Results are shown in Table 5 as percent RNA expression relative to cells that received no ASO treatment. "UTC" means untransfected control that was not transfected with siRNA (but may have been transfected with Isis No. 582801). As shown in Table 5, reduction of paraspeckle protein P54nrb expression prior to PS-ASO treatment resulted in greater PTEN PS-ASO activity than that achieved with treatment of the PS-ASO alone. These results, along with results in examples above, show that reducing the expression of paraspeckle proteins increased the activity of both 2'-MOE and 2'-cEt modified PS-ASOs.

TABLE 5

PTEN mRNA Expression

| Isis No. 582801 Concentration (nM) | siRNA Target | PTEN mRNA (%) |
|---|---|---|
| 0 | UTC | 100.00 |
| 0 | P54nrb | 100.00 |
| 1.5625 | UTC | 84.24 |
| 1.5625 | P54nrb | 67.07 |
| 3.125 | UTC | 75.81 |
| 3.125 | P54nrb | 59.31 |
| 6.25 | UTC | 53.36 |
| 6.25 | P54nrb | 52.70 |
| 12.5 | UTC | 40.18 |
| 12.5 | P54nrb | 46.38 |
| 25 | UTC | 30.84 |
| 25 | P54nrb | 37.52 |

Example 7

Increased PTEN PS-ASO Activity Following Reduction of PS-ASO Associating Protein Expression In order to continue to test the effect that PS-ASO associating proteins have on the activity of PS-ASO in cells, the activity of a PS-ASO targeting PTEN was analyzed following reduction of expression of Ku70 or Ku80. HeLa cells were plated and treated as described in Example 3, except Isis No. 116847 targeting PTEN, was used instead of Isis No. 110074. Results are shown in Tables 6 and 7 as percent RNA expression relative to cells that received no ASO treatment. "UTC" means untransfected control cells that were not transfected with siRNA (but may have been transfected with Isis No. 116847). As shown in Tables 6 and 7, reduction of Ku70 and Ku80 expression prior to PTEN PS-ASO treatment resulted in greater PS-ASO activity than that achieved with treatment of the PS-ASO alone or the activity achieved following reduction of LRPPRC expression.

TABLE 6

PTEN mRNA Expression

| Isis No. 116847 Concentration (nM) | siRNA Target | PTEN mRNA (%) |
|---|---|---|
| 0 | UTC | 100.00 |
| 0 | Ku70 | 100.00 |
| 0 | Ku80 | 100.00 |
| 0 | LRPPRC | 100.00 |
| 1.9 | UTC | 84.52 |
| 1.9 | Ku70 | 70.48 |
| 1.9 | Ku80 | 67.39 |
| 1.9 | LRPPRC | 81.59 |
| 3.75 | UTC | 66.27 |
| 3.75 | Ku70 | 52.55 |
| 3.75 | Ku80 | 52.79 |
| 3.75 | LRPPRC | 63.73 |
| 7.5 | UTC | 55.74 |
| 7.5 | Ku70 | 36.31 |
| 7.5 | Ku80 | 41.59 |
| 7.5 | LRPPRC | 52.14 |
| 15 | UTC | 30.77 |
| 15 | Ku70 | 21.27 |
| 15 | Ku80 | 21.69 |
| 15 | LRPPRC | 32.52 |
| 30 | UTC | 15.69 |
| 30 | Ku70 | 10.39 |
| 30 | Ku80 | 10.27 |
| 30 | LRPPRC | 12.64 |

TABLE 7

PTEN mRNA Expression

| Isis No. 116847 Concentration (nM) | siRNA Target | PTEN mRNA (%) |
|---|---|---|
| 0 | UTC | 100.00 |
| 0 | Ku70 | 100.00 |
| 0 | LRPPRC | 100.00 |
| 3.125 | UTC | 89.19 |
| 3.125 | Ku70 | 75.33 |
| 3.125 | LRPPRC | 88.05 |
| 6.25 | UTC | 76.10 |
| 6.25 | Ku70 | 55.71 |
| 6.25 | LRPPRC | 75.95 |
| 12.5 | UTC | 45.91 |
| 12.5 | Ku70 | 36.99 |
| 12.5 | LRPPRC | 38.85 |
| 25 | UTC | 26.59 |
| 25 | Ku70 | 21.37 |
| 25 | LRPPRC | 25.20 |

Example 8

Decreased PTEN PS-ASO Activity Following Reduction of PS-ASO Associating Protein Expression In order to test the possibility that additional PS-ASO associating proteins affect the activity of PS-ASOs in cells, the activity of Isis No. 116847 targeting PTEN was analyzed following reduction of expression of La, NPM1, ANXA2, or TCP1-beta. Reduction of expression of NCL1 or LRPPRC was also performed as a control. Both siRNAs and ASOs were used to reduce the expression of La and NPM1 to confirm that modulation of PS-ASO activity is independent of the mechanism of reduction of PS-ASO associating protein expression. HeLa cells were plated and treated as described in Example 3, except siRNA targeting La (cat. #HSS186106 or HSS186107, Life Technologies), NPM1 (cat. #s9676 or s9677, Life Technologies), or NCL1 (cat. #s9312 or s9313, Life Technologies) or an ASO targeting La (5-10-5 MOE full PS gapmer with 5-methylcytosines TTTTGGCAAAGTAATCGTCC, SEQ ID NO: 8, Isis No. 286529) or NPM1 (5-10-5 MOE full PS gapmer with 5-methylcytosines TAAAGTGATAATCTTTGTCG, SEQ ID NO: 9, Isis No. 573658) was used in the initial transfection, and Isis No. 116847 was used in the second transfection. Results are shown in Tables 8-12 as percent RNA expression relative to cells that received no ASO treatment. "UTC" means untransfected control cells that were not transfected in the first transfection (but may have been transfected with Isis No. 116847). As shown in Tables 8-12, reduction of La, NPM1, ANXA2, or TCP1-beta expression prior to PTEN PS-ASO treatment resulted in decreased PS-ASO activity than that achieved with treatment of the PS-ASO alone or the activity achieved following reduction of expression of a control protein. Thus, La, NPM1, ANXA2, and TCP1-beta were identified as enhancer proteins of PS-ASO activity.

TABLE 8

PTEN mRNA Expression

| Isis No. 116847 Concentration (nM) | siRNA or ASO/Target | PTEN mRNA (%) |
|---|---|---|
| 0 | UTC | 100.00 |
| 0 | La siRNA | 100.00 |
| 0 | NPM1 siRNA | 100.00 |
| 0 | NCL1 siRNA | 100.00 |
| 2.5 | UTC | 57.89 |
| 2.5 | La siRNA | 95.28 |
| 2.5 | NPM1 siRNA | 90.14 |
| 2.5 | NCL1 siRNA | 56.44 |
| 5 | UTC | 46.33 |
| 5 | La siRNA | 77.34 |
| 5 | NPM1 siRNA | 78.15 |
| 5 | NCL1 siRNA | 40.85 |
| 10 | UTC | 43.34 |
| 10 | La siRNA | 66.11 |
| 10 | NPM1 siRNA | 55.77 |
| 10 | NCL1 siRNA | 41.14 |
| 20 | UTC | 39.61 |
| 20 | La siRNA | 47.49 |
| 20 | NPM1 siRNA | 52.86 |
| 20 | NCL1 siRNA | 49.68 |
| 40 | UTC | 22.84 |
| 40 | La siRNA | 26.36 |
| 40 | NPM1 siRNA | 39.63 |
| 40 | NCL1 siRNA | 21.48 |

TABLE 9

PTEN mRNA Expression

| Isis No. 116847 Concentration (nM) | siRNA or ASO/Target | PTEN mRNA (%) |
|---|---|---|
| 0 | UTC | 100 |
| 0 | La siRNA | 100 |
| 0 | La ASO | 100 |
| 3.125 | UTC | 99 |
| 3.125 | La siRNA | 102 |
| 3.125 | La ASO | 91 |
| 6.25 | UTC | 64 |
| 6.25 | La siRNA | 86 |
| 6.25 | La ASO | 94 |
| 12.5 | UTC | 54 |
| 12.5 | La siRNA | 85 |
| 12.5 | La ASO | 72 |
| 25 | UTC | 47 |
| 25 | La siRNA | 62 |
| 25 | La ASO | 52 |
| 50 | UTC | 30 |

TABLE 9-continued

PTEN mRNA Expression

| Isis No. 116847 Concentration (nM) | siRNA or ASO/Target | PTEN mRNA (%) |
|---|---|---|
| 50 | La siRNA | 28 |
| 50 | La ASO | 26 |

TABLE 10

PTEN mRNA Expression

| Isis No. 116847 Concentration (nM) | siRNA or ASO/Target | PTEN mRNA (%) |
|---|---|---|
| 0 | UTC | 100 |
| 0 | NPM1 siRNA | 100 |
| 0 | NPM1 ASO | 100 |
| 3.125 | UTC | 100 |
| 3.125 | NPM1 siRNA | 99 |
| 3.125 | NPM1 ASO | 110 |
| 6.25 | UTC | 63 |
| 6.25 | NPM1 siRNA | 93 |
| 6.25 | NPM1 ASO | 90 |
| 12.5 | UTC | 54 |
| 12.5 | NPM1 siRNA | 78 |
| 12.5 | NPM1 ASO | 79 |
| 25 | UTC | 48 |
| 25 | NPM1 siRNA | 78 |
| 25 | NPM1 ASO | 47 |
| 50 | UTC | 31 |
| 50 | NPM1 siRNA | 37 |
| 50 | NPM1 ASO | 29 |

TABLE 11

PTEN mRNA Expression

| Isis No. 116847 Concentration (nM) | siRNA or ASO/Target | PTEN mRNA (%) |
|---|---|---|
| 0 | UTC | 100.00 |
| 0 | ANXA2 siRNA | 100.00 |
| 0 | LRPPRC siRNA | 100.00 |
| 3.125 | UTC | 87.72 |
| 3.125 | ANXA2 siRNA | 83.56 |
| 3.125 | LRPPRC siRNA | 77.50 |
| 6.25 | UTC | 51.75 |
| 6.25 | ANXA2 siRNA | 72.49 |
| 6.25 | LRPPRC siRNA | 56.76 |
| 12.5 | UTC | 34.61 |
| 12.5 | ANXA2 siRNA | 49.83 |
| 12.5 | LRPPRC siRNA | 38.24 |
| 25 | UTC | 30.23 |
| 25 | ANXA2 siRNA | 44.36 |
| 25 | LRPPRC siRNA | 31.88 |
| 50 | UTC | 29.92 |
| 50 | ANXA2 siRNA | 42.44 |
| 50 | LRPPRC siRNA | 33.61 |

TABLE 12

PTEN mRNA Expression

| Isis No. 116847 Concentration (nM) | siRNA or ASO/Target | PTEN mRNA (%) |
|---|---|---|
| 0 | UTC | 100.00 |
| 0 | TCP1-beta siRNA | 100.00 |
| 0 | LRPPRC siRNA | 100.00 |
| 3.125 | UTC | 89.19 |
| 3.125 | TCP1-beta siRNA | 103.14 |
| 3.125 | LRPPRC siRNA | 88.05 |
| 6.25 | UTC | 76.10 |
| 6.25 | TCP1-beta siRNA | 87.89 |
| 6.25 | LRPPRC siRNA | 75.95 |
| 12.5 | UTC | 45.91 |
| 12.5 | TCP1-beta siRNA | 50.55 |
| 12.5 | LRPPRC siRNA | 38.85 |
| 25 | UTC | 26.59 |
| 25 | TCP1-beta siRNA | 37.01 |
| 25 | LRPPRC siRNA | 25.20 |

Example 9

Decreased Drosha PS-ASO Activity Following Reduction of PS-ASO Associating Protein Expression In order to test the effect that PS-ASO associating proteins have on the activity of another PS-ASO in cells, the activity of Isis No. 25690 (5-10-5 MOE full PS gapmer with 5-methylcytosines ATCCCTTTCTTCCGCATGTG, SEQ ID NO: 10) targeting Drosha was analyzed following reduction of expression of La, NPM1, or VARS. Reduction of expression of NCL1 was performed as a control. The siRNA targeting VARS was purchased from Life Technologies (cat. #139607, "si7" or 139608, "si8"). HeLa cells were plated and treated as described in Examples 3 and 8, except siRNA targeting La, NPM1, VARS, or NCL1 was used in the initial transfection, and Isis No. 25690 was used in the second transfection. Results are shown in Tables 13 and 14 as percent RNA expression relative to cells that received no ASO treatment. "UTC" means untransfected control cells that were not transfected in the first transfection (but may have been transfected with Isis No. 25690). As shown in Tables 13 and 14, reduction of La, NPM1, or VARS expression prior to Drosha PS-ASO treatment resulted in decreased PS-ASO activity than that achieved with treatment of the PS-ASO alone or the activity achieved following reduction of expression of a control protein. Thus, La, NPM1, and VARS were identified as enhancer proteins of PS-ASO activity.

TABLE 13

Drosha mRNA Expression

| Isis No. 25690 Concentration (nM) | siRNA Target | Drosha mRNA (%) |
|---|---|---|
| 0 | UTC | 100.00 |
| 0 | La | 100.0 |
| 0 | NPM1 | 100.00 |
| 0 | NCL1 | 100.00 |
| 0.625 | UTC | 63.76 |
| 0.625 | La | 81.74 |
| 0.625 | NPM1 | 84.29 |
| 0.625 | NCL1 | 67.95 |
| 1.25 | UTC | 59.73 |
| 1.25 | La | 72.68 |
| 1.25 | NPM1 | 69.62 |
| 1.25 | NCL1 | 61.64 |
| 2.5 | UTC | 57.90 |
| 2.5 | La | 72.65 |
| 2.5 | NPM1 | 70.65 |
| 2.5 | NCL1 | 59.89 |
| 5 | UTC | 51.55 |

TABLE 13-continued

Drosha mRNA Expression

| Isis No. 25690 Concentration (nM) | siRNA Target | Drosha mRNA (%) |
|---|---|---|
| 5 | La | 59.82 |
| 5 | NPM1 | 63.19 |
| 5 | NCL1 | 50.96 |
| 10 | UTC | 47.36 |
| 10 | La | 57.22 |
| 10 | NPM1 | 56.14 |
| 10 | NCL1 | 38.91 |

TABLE 14

Drosha mRNA Expression

| Isis No. 25690 Concentration (nM) | siRNA | Drosha mRNA (%) |
|---|---|---|
| 0 | UTC | 100.00 |
| 0 | VARS si7 | 100.00 |
| 0 | VARS si8 | 100.00 |
| 3.125 | UTC | 56.72 |
| 3.125 | VARS si7 | 76.51 |
| 3.125 | VARS si8 | 70.14 |
| 6.25 | UTC | 47.59 |
| 6.25 | VARS si7 | 65.05 |
| 6.25 | VARS si8 | 60.45 |
| 12.5 | UTC | 37.98 |
| 12.5 | VARS si7 | 58.40 |
| 12.5 | VARS si8 | 49.30 |
| 25 | UTC | 26.09 |
| 25 | VARS si7 | 48.10 |
| 25 | VARS si8 | 37.28 |
| 50 | UTC | 18.59 |
| 50 | VARS si7 | 30.99 |
| 50 | VARS si8 | 25.02 |

Example 10

Decreased NCL1 PS-ASO Activity Following Reduction of PS-ASO Associating Protein Expression In order to test the effect that PS-ASO associating proteins have on the activity of another PS-ASO in cells, the activity of Isis No. 110074 targeting NCL1 was analyzed following reduction of expression of La, NPM1, ANXA2, or VARS. Reduction of expression of LRPPRC was performed as a control. HeLa cells were plated and treated as described in Examples 3, 8, and 9. Results are shown in Tables 15-17 as percent RNA expression relative to cells that received no ASO treatment. "UTC" means untransfected control cells that were not transfected in the first transfection (but may have been transfected with Isis No. 110074). As shown in Tables 15-17, reduction of La, NPM1, ANXA2, or VARS expression prior to NCL1 PS-ASO treatment resulted in decreased PS-ASO activity than that achieved with treatment of the PS-ASO alone or the activity achieved following reduction of expression of a control protein. Thus, La, NPM1, ANXA2, and VARS were confirmed as general enhancer proteins of PS-ASO activity.

TABLE 15

NCL1 mRNA Expression

| Isis No. 110074 Concentration (nM) | siRNA | NCL1 mRNA (%) |
|---|---|---|
| 0 | UTC | 100.00 |
| 0 | La | 100.00 |
| 0 | NPM1 | 100.00 |
| 3.125 | UTC | 71.82 |
| 3.125 | La | 79.93 |
| 3.125 | NPM1 | 77.32 |
| 6.25 | UTC | 58.78 |
| 6.25 | La | 77.65 |
| 6.25 | NPM1 | 70.28 |
| 12.5 | UTC | 34.99 |
| 12.5 | La | 58.34 |
| 12.5 | NPM1 | 45.86 |
| 25 | UTC | 14.31 |
| 25 | La | 22.84 |
| 25 | NPM1 | 41.72 |
| 50 | UTC | 13.59 |
| 50 | La | 30.61 |
| 50 | NPM1 | 20.41 |

TABLE 16

NCL1 mRNA Expression

| Isis No. 110074 Concentration (nM) | siRNA | NCL1 mRNA (%) |
|---|---|---|
| 0 | UTC | 100.00 |
| 0 | ANXA2 | 100.00 |
| 0 | LRPPRC | 100.00 |
| 2.5 | UTC | 75.98 |
| 2.5 | ANXA2 | 93.01 |
| 2.5 | LRPPRC | 72.17 |
| 5 | UTC | 67.56 |
| 5 | ANXA2 | 86.25 |
| 5 | LRPPRC | 66.65 |
| 10 | UTC | 45.80 |
| 10 | ANXA2 | 68.28 |
| 10 | LRPPRC | 49.77 |
| 20 | UTC | 24.04 |
| 20 | ANXA2 | 33.96 |
| 20 | LRPPRC | 28.55 |
| 40 | UTC | 12.70 |
| 40 | ANXA2 | 21.51 |
| 40 | LRPPRC | 16.87 |

TABLE 17

NCL1 mRNA Expression

| Isis No. 110074 Concentration (nM) | siRNA | NCL1 mRNA (%) |
|---|---|---|
| 0 | UTC | 100.00 |
| 0 | VARS si7 | 100.00 |
| 0 | VARS si8 | 100.00 |
| 3.125 | UTC | 54.11 |
| 3.125 | VARS si7 | 59.89 |
| 3.125 | VARS si8 | 72.98 |
| 6.25 | UTC | 43.14 |
| 6.25 | VARS si7 | 52.36 |
| 6.25 | VARS si8 | 56.09 |
| 12.5 | UTC | 26.56 |
| 12.5 | VARS si7 | 37.54 |
| 12.5 | VARS si8 | 35.69 |
| 25 | UTC | 12.96 |
| 25 | VARS si7 | 22.43 |
| 25 | VARS si8 | 18.09 |
| 50 | UTC | 6.91 |

TABLE 17-continued

NCL1 mRNA Expression

| Isis No. 110074 Concentration (nM) | siRNA | NCL1 mRNA (%) |
|---|---|---|
| 50 | VARS si7 | 12.07 |
| 50 | VARS si8 | 11.14 |

Example 11

Decreased U16 PS-ASO Activity Following Reduction of PS-ASO Associating Protein Expression In order to test the effect that PS-ASO associating proteins have on the activity of another PS-ASO in cells, the activity of Isis No. 462026 targeting U16 was analyzed following reduction of expression of La, NPM1, ANXA2, or VARS. Reduction of expression of LRPPRC was performed as a control. HeLa cells were plated and treated as described in Examples 3, 8, and 9. Results are shown in Tables 18-20 as percent RNA expression relative to cells that received no ASO treatment. "UTC" means untransfected control cells that were not transfected in the first transfection (but may have been transfected with Isis No. 462026). As shown in Tables 18-20, reduction of La, NPM1, ANXA2, or VARS expression prior to U16 PS-ASO treatment resulted in decreased PS-ASO activity than that achieved with treatment of the PS-ASO alone or the activity achieved following reduction of expression of a control protein. Thus, La, NPM1, ANXA2, and VARS were confirmed as general enhancer proteins of PS-ASO activity.

TABLE 18

U16 snoRNA Expression

| Isis No. 462026 Concentration (nM) | siRNA | U16 snoRNA (%) |
|---|---|---|
| 0 | UTC | 100.00 |
| 0 | La | 100.00 |
| 0 | NPM1 | 100.00 |
| 1.25 | UTC | 66.60 |
| 1.25 | La | 85.99 |
| 1.25 | NPM1 | 94.55 |
| 2.5 | UTC | 58.31 |
| 2.5 | La | 75.20 |
| 2.5 | NPM1 | 67.59 |
| 5 | UTC | 51.72 |
| 5 | La | 70.02 |
| 5 | NPM1 | 60.59 |
| 10 | UTC | 40.10 |
| 10 | La | 60.26 |
| 10 | NPM1 | 49.67 |
| 20 | UTC | 35.35 |
| 20 | La | 51.83 |
| 20 | NPM1 | 50.04 |

TABLE 19

U16 snoRNA Expression

| Isis No. 462026 Concentration (nM) | siRNA | U16 snoRNA (%) |
|---|---|---|
| 0 | UTC | 100.00 |
| 0 | ANXA2 | 100.00 |
| 0 | LRPPRC | 100.00 |

TABLE 19-continued

U16 snoRNA Expression

| Isis No. 462026 Concentration (nM) | siRNA | U16 snoRNA (%) |
|---|---|---|
| 1.6 | UTC | 66.13 |
| 1.6 | ANXA2 | 81.19 |
| 1.6 | LRPPRC | 61.15 |
| 3.125 | UTC | 54.01 |
| 3.125 | ANXA2 | 72.44 |
| 3.125 | LRPPRC | 52.46 |
| 6.25 | UTC | 48.08 |
| 6.25 | ANXA2 | 59.82 |
| 6.25 | LRPPRC | 36.41 |
| 12.5 | UTC | 23.95 |
| 12.5 | ANXA2 | 40.28 |
| 12.5 | LRPPRC | 23.84 |
| 25 | UTC | 21.62 |
| 25 | ANXA2 | 29.81 |
| 25 | LRPPRC | 14.52 |

TABLE 20

U16 snoRNA Expression

| Isis No. 462026 Concentration (nM) | siRNA | U16 snoRNA (%) |
|---|---|---|
| 0 | UTC | 100.00 |
| 0 | VARS si7 | 100.00 |
| 0 | VARS si8 | 100.00 |
| 1.5625 | UTC | 44.37 |
| 1.5625 | VARS si7 | 64.25 |
| 1.5625 | VARS si8 | 76.65 |
| 3.125 | UTC | 32.54 |
| 3.125 | VARS si7 | 50.13 |
| 3.125 | VARS si8 | 62.87 |
| 6.25 | UTC | 16.33 |
| 6.25 | VARS si7 | 35.75 |
| 6.25 | VARS si8 | 33.30 |
| 12.5 | UTC | 8.17 |
| 12.5 | VARS si7 | 21.11 |
| 12.5 | VARS si8 | 15346 |
| 25 | UTC | 7.15 |
| 25 | VARS si7 | 15.17 |
| 25 | VARS si8 | 9.70 |

Example 12

Increased PTEN PS-ASO Activity Following Increase of PS-ASO Associating Protein Expression In order to further test the effect that enhancer PS-ASO associating proteins have on the activity of PS-ASO in cells, the activity of Isis No. 116847 targeting PTEN was analyzed following over-expression of La or NPM1. HeLa cells were plated in 6-well dishes and grown to 70% confluency, then transfected with a plasmid purchased from Genecopoeia to over-express La (cat. #EX-G0043-M02) or NPM1 (cat. #EX-Z2182-M02). 48 hours after plasmid transfection, the cells were transfected with Isis No. 116847 using Lipofectamine 2000 (Life Technologies) at 4 µg/mL final concentration. Cells were harvested for RNA extraction 4 hours after transfection with Isis No. 116847, and PTEN mRNA levels were analyzed via RT-PCR. Results are shown in Table 21 as percent RNA expression relative to cells that received no ASO treatment. "UTC" means untransfected control cells that were not transfected in the first transfection (but may have been transfected with Isis No. 116847). As shown in Table 21, over-expression of La or NPM1 prior to PTEN PS-ASO treatment resulted in increased PS-ASO activity than that achieved with treatment of the PS-ASO alone. Thus, La and NPM1 were further confirmed as general enhancer proteins of PS-ASO activity.

TABLE 21

PTEN mRNA Expression

| Isis No. 116847 Concentration (nM) | Plasmid | PTEN mRNA (%) |
|---|---|---|
| 0 | UTC | 100.0 |
| 0 | La | 100.0 |
| 0 | NPM1 | 100.0 |
| 1.875 | UTC | 69.2 |
| 1.875 | La | 68.3 |
| 1.875 | NPM1 | 70.4 |
| 3.75 | UTC | 60.5 |
| 3.75 | La | 47.4 |
| 3.75 | NPM1 | 53.1 |
| 7.5 | UTC | 49.2 |
| 7.5 | La | 38.6 |
| 7.5 | NPM1 | 38.1 |
| 15 | UTC | 39.5 |
| 15 | La | 24.3 |
| 15 | NPM1 | 24.1 |
| 30 | UTC | 30.1 |
| 30 | La | 24.5 |
| 30 | NPM1 | 20.6 |

Example 13

Increased NCL1 PS-ASO Activity Following Increase of PS-ASO Associating Protein Expression In order to further test the effect that enhancer PS-ASO associating proteins have on the activity of another PS-ASO in cells, the activity of Isis No. 110074 targeting NCL1 was analyzed following over-expression of La or NPM1. HeLa cells were plated and treated as described in Example 12, except Isis No. 110074 was used in the second transfection. Results are shown in Table 22 as percent RNA expression relative to cells that received no ASO treatment. "UTC" means untransfected control cells that were not transfected in the first transfection (but may have been transfected with Isis No. 110074). As shown in Table 22, over-expression of La or NPM1 prior to NCL1 PS-ASO treatment resulted in increased PS-ASO activity than that achieved with treatment of the PS-ASO alone. Thus, La and NPM1 were further confirmed as general enhancer proteins of PS-ASO activity.

TABLE 22

NCL1 mRNA Expression

| Isis No. 110074 Concentration (nM) | Plasmid | NCL1 mRNA (%) |
|---|---|---|
| 0 | UTC | 100 |
| 0 | La | 100 |
| 0 | NPM1 | 100 |
| 1.875 | UTC | 74 |
| 1.875 | La | 60 |
| 1.875 | NPM1 | 61 |
| 3.75 | UTC | 58 |
| 3.75 | La | 39 |
| 3.75 | NPM1 | 44 |
| 7.5 | UTC | 42 |
| 7.5 | La | 20 |
| 7.5 | NPM1 | 22 |
| 15 | UTC | 38 |
| 15 | La | 12 |
| 15 | NPM1 | 13 |

TABLE 22-continued

NCL1 mRNA Expression

| Isis No. 110074 Concentration (nM) | Plasmid | NCL1 mRNA (%) |
|---|---|---|
| 30 | UTC | 31 |
| 30 | La | 8 |
| 30 | NPM1 | 8 |

Example 14

Decreased NCL1 PS-ASO Activity Following Reduction of PS-ASO Associating Protein Expression In order to test the possibility that TCP1 complex proteins that associate with PS-ASOs affect the activity of PS-ASOs in cells, the activity of Isis No. 110074 targeting NCL1 was analyzed following reduction of expression of TCP1-alpha, TCP1-beta, or TCP1-epsilon. HeLa cells were plated and treated as described in Example 8, except siRNA targeting TCP1-alpha (cat. #s224715, Ambion), TCP1-beta (cat. #s20756, Ambion), or TCP1-epsilon (cat. #19566 or 136414, Ambion) was used in the initial transfection, and Isis No. 110074 was used in the second transfection. Results are shown in Table 23 as percent RNA expression relative to cells that received no ASO treatment. "UTC" means untransfected control cells that were not transfected in the first transfection (but may have been transfected with Isis No. 110074). As shown in Table 23, reduction of TCP1-alpha, TCP1-beta, or TCP1-epsilon expression prior to NCL1 PS-ASO treatment resulted in decreased PS-ASO activity than that achieved with treatment of the PS-ASO alone or the activity achieved following reduction of expression of a control protein. Thus, TCP1-alpha, TCP1-beta, and TCP1-epsilon were identified as enhancer proteins of PS-ASO activity.

TABLE 23

NCL1 mRNA Expression

| Isis No. 110074 Concentration (nM) | siRNA Target | NCL1 mRNA (%) |
|---|---|---|
| 0 | UTC | 100.00 |
| 0 | TCP1-alpha | 100.00 |
| 0 | TCP1-beta | 100.00 |
| 0 | TCP1-epsilon | 100.0 |
| 3.125 | UTC | 53.71 |
| 3.125 | TCP1-alpha | 76.76 |
| 3.125 | TCP1-beta | 74.34 |
| 3.125 | TCP1-epsilon | 73.65 |
| 6.25 | UTC | 33.13 |
| 6.25 | TCP1-alpha | 46.16 |
| 6.25 | TCP1-beta | 52.39 |
| 6.25 | TCP1-epsilon | 53.46 |
| 12.5 | UTC | 16.62 |
| 12.5 | TCP1-alpha | 22.95 |
| 12.5 | TCP1-beta | 28.27 |
| 12.5 | TCP1-epsilon | 25.75 |
| 25 | UTC | 7.29 |
| 25 | TCP1-alpha | 10.98 |
| 25 | TCP1-beta | 11.13 |
| 25 | TCP1-epsilon | 7.40 |
| 50 | UTC | 3.53 |
| 50 | TCP1-alpha | 5.21 |
| 50 | TCP1-beta | 7.00 |
| 50 | TCP1-epsilon | 5.95 |

Example 15

Decreased Malat1 PS-ASO Activity Following Reduction of PS-ASO Associating Protein Expression In order to test the possibility that TCP1 complex proteins that associate with PS-ASOs affect the activity of another PS-ASOs in cells, the activity of Isis No. 395254 targeting Malat1 was analyzed following reduction of expression of TCP1-alpha, TCP1-beta, or TCP1-epsilon. HeLa cells were plated and treated as described in Example 14, except Isis No. 110074 was used in the second transfection. Results are shown in Table 24 as percent RNA expression relative to cells that received no ASO treatment. "UTC" means untransfected control cells that were not transfected in the first transfection (but may have been transfected with Isis No. 395254). As shown in Table 24, reduction of TCP1-alpha, TCP1-beta, or TCP1-epsilon expression prior to Malat1 PS-ASO treatment resulted in decreased PS-ASO activity than that achieved with treatment of the PS-ASO alone or the activity achieved following reduction of expression of a control protein. Thus, TCP1-alpha, TCP1-beta, and TCP1-epsilon were identified as general enhancer proteins of PS-ASO activity.

TABLE 24

Malat1 Expression

| Isis No. 395254 Concentration (nM) | siRNA Target | Malat1 RNA (%) |
|---|---|---|
| 0 | UTC | 100.00 |
| 0 | TCP1-alpha | 100.00 |
| 0 | TCP1-beta | 100.00 |
| 0 | TCP1-epsilon | 100.0 |
| 1.55 | UTC | 41.56 |
| 1.55 | TCP1-alpha | 52.03 |
| 1.55 | TCP1-beta | 62.08 |
| 1.55 | TCP1-epsilon | 58.79 |
| 3.125 | UTC | 32.48 |
| 3.125 | TCP1-alpha | 42.11 |
| 3.125 | TCP1-beta | 43.84 |
| 3.125 | TCP1-epsilon | 50.15 |
| 6.25 | UTC | 18.71 |
| 6.25 | TCP1-alpha | 26.49 |
| 6.25 | TCP1-beta | 30.19 |
| 6.25 | TCP1-epsilon | 35.77 |
| 12.5 | UTC | 20.03 |
| 12.5 | TCP1-alpha | 20.97 |
| 12.5 | TCP1-beta | 30.78 |
| 12.5 | TCP1-epsilon | 26.97 |
| 25 | UTC | 16.22 |
| 25 | TCP1-alpha | 20.24 |
| 25 | TCP1-beta | 26.22 |
| 25 | TCP1-epsilon | 20.78 |

Example 16

Determination of the Binding Constant of Hsp90 to ASOs

To determine the binding constant of Hsp90 to ASOs, a PS/cEt ASO (Isis No. 586183) or a PS/LNA ASO (Isis No. 586184) were radiolabeled and incubated with different concentrations of purified Hsp90α protein. Isis No. 586183 has the following sequence (CTGCTAGCCTCTG-GATTTGA, SEQ ID NO: 2) and Isis No. 586184 has the following sequence (CTGCTAGCCTCTGGATTTGA, SEQ ID NO: 2). Isis Numbers 586183 and 586184 are biotinylated 5-10-5 gapmers, in which each nucleotide in the wings is cEt modified (Isis No. 586183) or LNA modified (Isis No. 586184) and each nucleotide in the gap is 2'-deoxy. All cytosines are 5-methylcytosines and all internucleoside linkages are phosphorothioate (PS). The 5'-ends are biotinylated via a tetraethyleneglycol linker.

The protein-bound ASOs were transferred to a nitrocellulose membrane and the signal intensity was determined. As a control, no significant binding was found for a PS/DNA ASO. The specific binding of protein-bound ASO to the nitrocellulose membrane was confirmed using a double-filter binding assay for PS/cEt and PS/LNA ASOs. The unbound ASOs were attracted using a Hybond-N+Nylon membrane under the Hybond ECL nitrocellulose membrane. The bound-ASO signal intensity was quantified and plotted using Prism and the binding constant to PS/cEt and PS/LNA was determined to be 19.7 nM and 17.7 nM, respectively. Together, these results indicate that Hsp90 protein directly interacts with PS/cEt and PS/LNA ASOs, and that such an interaction is not unique to a particular ASO sequence.

Example 17

Reduction of Hsp90 Protein Inhibits the Antisense Activity of ASOs

To determine if Hsp90 protein influences the antisense activity of ASOs, the effect of reducing Hsp90β protein, which is constitutively expressed in cells, was analyzed. Both Hsp90β mRNA and protein were significantly reduced by siRNA treatment in HeLa cells, as determined by qRT-PCR and western analysis, respectively. Next, control or Hsp90β reduced cells were transfected with PS-ASOs with 5'-cEt+3'-MOE (Isis No. 598343) or 5'-MOE+3'-cEt (Isis No. 598341) wings. These ASOs have the same sequence complementary to a site in PTEN mRNA. 5'-cEt+3'-MOE (Isis No. 598343) is a 5-10-5 gapmer and has the nucleobase sequence CTGCTAGCCTCTGGATTTGA (SEQ ID NO. 2). Each of the 5 nucleobases in the 5'-wing are are cEt modified, each nucleoside in the gap is 2'-deoxy, and each of the 5 nucleobases in the 3'-wing are 2'-MOE. All cytosines are 5-methylcytosines and all internucleoside linkages are phosphorothioate (PS). 5'-MOE+3'-cEt (Isis No. 598341) is a 5-10-5 gapmer and has the nucleobase sequence CTGCTAGCCTCTGGATTTGA (SEQ ID NO. 2). Each of the 5 nucleobases in the 5'-wing are are 2'-MOE modified, each nucleoside in the gap is 2'-deoxy, and each of the 5 nucleobases in the 3'-wing are cEt modified. All cytosines are 5-methylcytosines and all internucleoside linkages are phosphorothioate (PS).

Four hours after ASO transfection, total RNA was prepared and PTEN mRNA levels were detected by qRT-PCR. The results showed that reduction of Hsp90β significantly inhibited the antisense activity of ASO 598343, but not ASO 598341, as indicated by less reduction of the PTEN mRNA in Hsp90β reduced cells.

The invention claimed is:

1. A method for increasing the antisense activity of an antisense compound in a cell, comprising:
    contacting the cell with an inhibitor of the amount or activity of a repressor protein that binds antisense compounds comprising a plurality of phosphorothioate internucleoside linkages in the cell;
    and subsequently contacting the cell with the antisense compound, wherein the target nucleic acid of the antisense compound does not code for the repressor protein, and wherein the antisense compound comprises a modified oligonucleotide that comprises a plurality of phosphorothioate internucleoside linkages.

2. The method of claim 1, wherein the inhibitor comprises a second antisense compound targeting a nucleic acid that codes for the repressor protein.

3. The method of claim 1, wherein the repressor protein is selected from Ku70, Ku80, hnRNPK, P54nrb, PSF, and PSPC1.

4. The method of claim 1, wherein the repressor protein is selected from Ku70 and Ku80.

5. The method of claim 1, wherein the repressor protein is selected from hnRNPK, P54nrb, PSF, and PSPC1.

6. The method of claim 1, wherein all of the internucleoside linkages of the antisense compound are phosphorothioate internucleoside linkages.

7. The method of claim 1, wherein the antisense compound comprises a gapmer.

8. The method of claim 1, wherein the antisense activity is reduction of the amount of a target nucleic acid of the antisense compound.

9. The method of claim 8, wherein the reduction of the amount of a target nucleic acid of the antisense compound is increased relative to the reduction that occurs when a cell is contacted with the antisense compound in the absence of the inhibitor of the amount or activity of a repressor protein in the cell.

10. The method of claim 1, wherein the antisense compound comprises at least one conjugate.

11. The method of claim 1, wherein the cell is in an animal.

12. The method of claim 11, wherein the animal is a human.

* * * * *